United States Patent [19]

Fomenko

[11] 4,057,351

[45] Nov. 8, 1977

[54] COHERENT SCANNING SYSTEM FOR FABRIC INSPECTION

[75] Inventor: Sergei Michael Fomenko, Woodland Hills, Calif.

[73] Assignee: Greenwood Mills, Inc., Greenwood, S.C.

[21] Appl. No.: 660,253

[22] Filed: Feb. 23, 1976

[51] Int. Cl.² .............................................. G01N 21/16
[52] U.S. Cl. ......................................... 356/238; 350/6; 350/7; 356/200
[58] Field of Search ................. 356/200, 238, 239, 71, 356/160; 350/6, 162 SF, 319, 7; 250/563, 571, 572; 26/70; 66/166

[56] References Cited

U.S. PATENT DOCUMENTS

| 3,657,727 | 4/1972 | Blevins | 26/70 |
| 3,659,950 | 5/1972 | Troll et al. | 356/200 |
| 3,709,610 | 1/1973 | Kruegle | 356/160 |

Primary Examiner—John K. Corbin
Assistant Examiner—B. Wm. de los Reyes
Attorney, Agent, or Firm—Cushman, Darby & Cushman

[57] ABSTRACT

A system is provided for scanning a laser beam across the width of fabric material to be inspected. A scanning mirror receives coherent light from the beam and is mounted to repeatedly swing through a given scan angle. An optical arrangement of mirrors in side-by-side relationship receives the light beam from the scanning mirror and directs it in successive side-by-side parallel directions or channels towards the fabric to irradiate successive areas of the fabric across its width. A de-scanning mirror is mounted to repeatedly swing through the same given scan angle in synchronism with the scanning mirror and a second optical arrangement of mirrors in alignment with the first mentioned mirrors receives the beam after passing through successive areas of the fabric and directs it to the de-scanning mirror. The beam reflected from the de-scanning mirror in turn can then be analyzed.

10 Claims, 6 Drawing Figures

COHERENT SCANNING SYSTEM FOR FABRIC INSPECTION

This invention relates to high speed automatic inspection of fabric from textile mills and more particularly to a coherent scanning system enabling large areas of fabric to be continuously and automatically inspected using a single coherent light beam.

BACKGROUND OF THE INVENTION

In the co-pending patent application of Donald Carleton Mead, Harvey Lee Kasdan and Jordan Lewis Dorrity entitled METHOD FOR AUTOMATIC FABRIC INSPECTION, Ser. No. 660,252 filed concurrently herewith and assigned to the same assignee as the present application, there is disclosed a basic method of fabric inspection by the analysis of diffraction patterns developed by a coherent light beam passed through the fabric.

In the method described in the foregoing application, the coherent light beam has a cross-sectional area sufficient to encompass a large number of warps and fillings making up the fabric so that a certain cross-sectional area of the fabric irradiated by the beam can be completely analyzed by appropriate detector means on the other side of the fabric. Further, if the fabric is moved in a plane normal to the direction of the beam, successive areas of the fabric can be continuously inspected, there being developed a time sequential diffraction pattern at the detector.

If the fabric material is fairly wide, a number of problems arise if it is desired to inspect the entire area of the fabric from one edge to the other. These problems primarily result from the fact that the cross-sectional area of the coherent beam is substantially smaller than the complete area of the fabric to be inspected.

If the coherent beam is expanded to cover the entire width of the web, either the energy levels fall below detectable levels or an impossibly high laser power is required. Further, the diameter of the transform lens or mirror must be as wide as the fabric thereby creating an extremely difficult lens design problem and cost. Most importantly, the beam diameter itself cannot be too large relative to the spacing of the warps and fillings in the fabric if defects are to be properly detected.

One solution would be to use a number of systems such as disclosed in the afore-mentioned patent application in side-by-side relationship to irradiate the entire width of the web. This solution is not particularly desirable since a large number of lasers, detectors and detector processing electronics would be required which is prohibitively complex and expensive.

Another possible solution would be to simply move the entire laser light beam generator from one edge of the fabric to the other while directing the beam at the fabric. However, this solution would be complicated from the mechanical standpoint and the fact that both the detector and laser beam source would have to be moved simultaneously and alignment problems would be difficult to maintain. Also, the speed of scanning in this manner would be relatively slow. On the other hand, if it is attempted to move the fabric transversely there are again encountered mechanical problems since normally a large bolt of fabric which may be hundreds of feet in length together with its transport means for moving the fabric downwardly would have to be moved. Again, any such scanning system of this type would be very slow.

BRIEF DESCRIPTION OF THE PRESENT INVENTION

With the foregoing in mind, the present invention contemplates a coherent scanning system which reconciles the foregoing difficulties.

More particularly, in accord with this invention a given area of fabric can be inspected by analysis of the diffraction pattern developed by a single coherent light beam passed through the fabric wherein the cross-sectional area of the light beam is substantially less than the given area to be inspected. The system for accomplishing this type of scanning includes a scanning mirror receiving the coherent light beam and mounted for repeated swinging through a given scan angle.

A plurality of first optical means in side-by-side relationship successively receives the light beam from the scanning mirror and direct it in successive side-by-side parallel directions towards the fabric to irradiate successive areas of the fabric covering the given area. A de-scanning mirror is provided on the other side of the fabric and mounted to repeatedly swing through the same given scan angle in synchronism with the scanning mirror. Cooperating with this de-scanning mirror is a plurality of second optical means in side-by-side relationship in alignment with the first optical means respectively for successively receiving the beam after passing through the successive areas of fabric and successively directing the beam to the de-scanning mirror as it swings through the scan angle.

The resulting beam reflected from the de-scanning mirror is then passed into suitable detector optics for analysis.

By locking the scanning and de-scanning mirrors both in frequency and phase, the light beam leaving the de-scanning mirror is subject only to a very slight motion during each successive reflection and can be easily detected. On the other hand, the entire width of the fabric material is scanned and this scanning of the width repeated as the fabric material moves downwardly.

In a preferred embodiment of the invention, a second scanning mirror together with suitable optics and a second de-scanning mirror, all constituting essentially a mirror image of the first scanning system are arranged to pass the coherent beam in an opposite direction through the fabric, successive areas of the fabric irradiated by this latter coherent beam falling between the first successive areas irradiated from the one side of the fabric whereby the fabric may be continuously scanned in one direction from one edge to the other while it is moving vertically to provide a complete 100% coverage.

BRIEF DESCRIPTION OF THE DRAWINGS

A better understanding of this invention will be had by now referring to the accompanying drawings in which.

DETAILED DESCRIPTION OF THE PREFERRED EMBODIMENT

Figure 1:
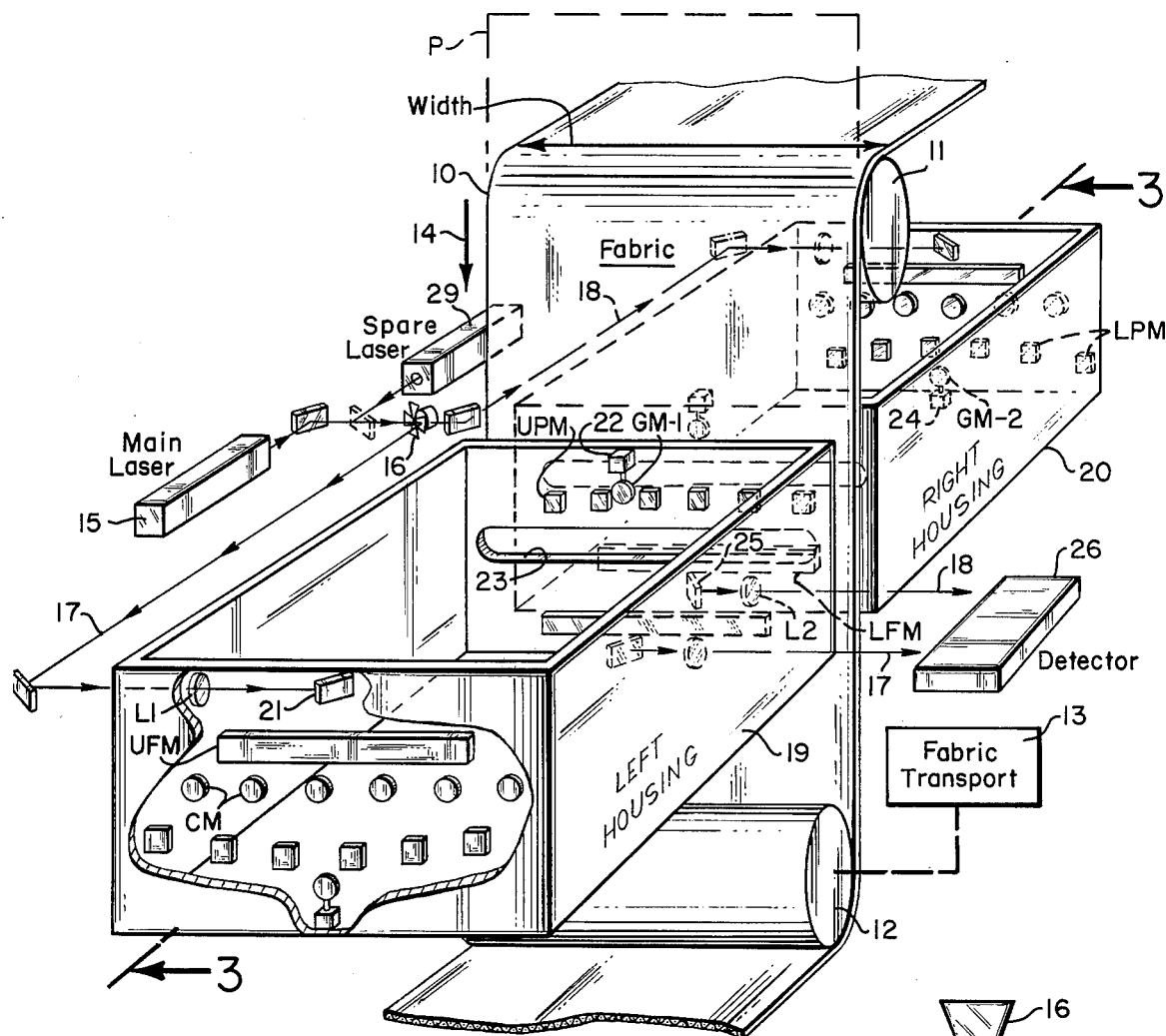
FIG. 1 is a highly schematic perspective view of basic components making up the coherent scanning system of this invention.

Referring first to FIG. 1, there is shown fabric 10 from a typical textile mill which is to be inspected for quality by the scanning system of this invention. As shown, the fabric passes over an upper roller 11 and thence extends downwardly to lie in a vertical plane P and thereafter passes under a lower roller 12. The fabric is caused to move vertically downwardly by a suitable fabric transport represented by the block 13, the downward movement being indicated by the arrow 14 beneath the numeral 10.

A coherent light beam source includes a main laser indicated in the upper left of FIG. 1 by the block 15 passing a beam of coherent light through a beam switch means 16 which essentially chops the coherent beam so that the beam is alternately passed in a leftward direction as indicated at 17 and a rightward direction as indicated at 18.

A left housing 19 is positioned on the left side of the vertical plane P and a right housing 20 is positioned on the right or opposite side of the vertical plane P.

As will become clearer as the description proceeds, the optical elements in the right housing 20 are the same as the optical elements in the left housing 19 but are oriented in opposite directions so that the components in the left and right housings are essentially mirror images of each other but slightly offset horizontally.

Considering first the various components in the left housing 19, there is provided a left scanning mirror GM-1 positioned centrally of the housing end closest to the fabric 10. A 45° mirror 21 receives the coherent light beam from an exterior 45° mirror and relay lens L1 and directs it to the scanning mirror GM-1. Means 22 mount the scanning mirror GM-1 for oscillating movement about a vertical axis through a given scan angle.

An upper fold mirror UFM, beneath the 45° mirror 21 receives the swinging beam from GM-1 and directs it successively to a plurality of individual left upper plane mirrors designated UPM positioned on a horizontal row beneath the scanning mirror GM-1 at the end of the housing.

Each of the upper plane mirrors UPM directs the beam in successive parallel directions generally normal to the vertical plane P as the scanning mirror swings through the given scan angle. These parallel directions or channels extend in side-by-side relationship for a distance corresponding to the width of the fabric 10 as will become clearer as the description proceeds.

Beneath the upper fold mirror UFM on the inside front end portion of the housing 19, there are provided a plurality of individual left concave mirrors CM positioned on a horizontal row in alignment with the parallel directions or channels of light reflected from the upper plane mirrors UPM such that these concave mirrors successively receive the light beam and direct the beam towards the vertical plane P. The end of the housing 19 adjacent to the fabric 10 has an elongated outlet slot 23 through which the beam passes such that successive area in a horizontal row across the width of the fabric 10 in the plane P are exposed to the light beam.

Referring to the lower interior portion of the right housing 20 as illustrated in phantom lines, there is provided a de-scanning mirror GM-2 and appropriate means 24 mounting the de-scanning mirror for oscillating the mirror about a vertical axis through the given scan angle in synchronism with the left scanning mirror GM-1. Provided above the de-scanning mirror GM-2 are a plurality of lower plane mirrors LPM in a horizontal row oriented to successively receive the light beam from the left concave mirrors CM in the left housing after passing through the fabric. These lower plane mirrors on the inside far wall of the right housing 20 reflect the light beam to a lower fold mirror LFM at the opposite end of the right housing 20 which in turn passes the beam to the de-scanning mirror GM-2 as it swings through the given scan angle.

The beam reflected from the de-scanning mirror GM-2 is diverted by a 45° mirror 25 laterally through a transform lens L2 out of the housing 20 to a detector 26.

As mentioned and as schematically shown in FIG. 1 although not specifically labelled, the right housing also includes a right scanning mirror receiving the coherent light beam 18 when passed thereto by the switch means 16, a plurality of individual right upper plane mirrors, an upper fold mirror, and a plurality of individual right concave mirrors all functioning in the same manner as the left scanning mirror, left upper plane mirrors UPM and left concave mirrors CM but facing in opposite directions and offset horizontally to successively pass the coherent beam through the vertical plane in an opposite direction. The arrangement is such that successive areas in a horizontal row across the width of the fabric in the plane P falling between the first mentioned successive areas respectively are exposed to the coherent light beam, the left housing including a de-scanning mirror, a lower fold mirror and a plurality of individual lower plane mirrors, all functioning in the same manner as the first mentioned de-scanning mirror GM-2 and first mentioned lower plane mirrors LPM but facing in opposite directions and offset horizontally to successively receive the coherent light beam after passing through the fabric in the opposite direction. This received light beam is reflected to the second mentioned de-scanning mirror and diverted out of the housing to the detector 26.

It will be understood, accordingly, that the upper portion of the left housing supports the left scanning components for passing the coherent beam 17 through the fabric in one direction while the right housing includes in its lower portion the de-scanning optical components for this beam after passing through the fabric. Similarly, the right housing includes in its upper portion scanning components for the coherent beam 18 when switched to pass into the right housing 20 and the lower interior of the left housing supports the de-scanning components for this latter mentioned beam.

Figure 2:
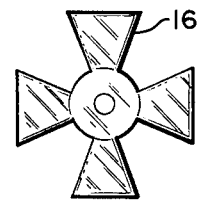
FIG. 2 is a front view of a beam switch means incorporated in the system of FIG. 1.

FIG. 2 shows the beam switch means 16 which essentially constitutes four mirrors mounted circumferentially at 90° and separated by a spacing equal to their widths such that when oriented for rotation in a plane at 45° to the beam from the main laser, the beam will alternately be reflected from the mirrors and pass between the mirrors of the switch 16 so that the coherent beams 17 and 18 described in FIG. 1 will be alternately directed to the left and right housings as described.

Figure 3:
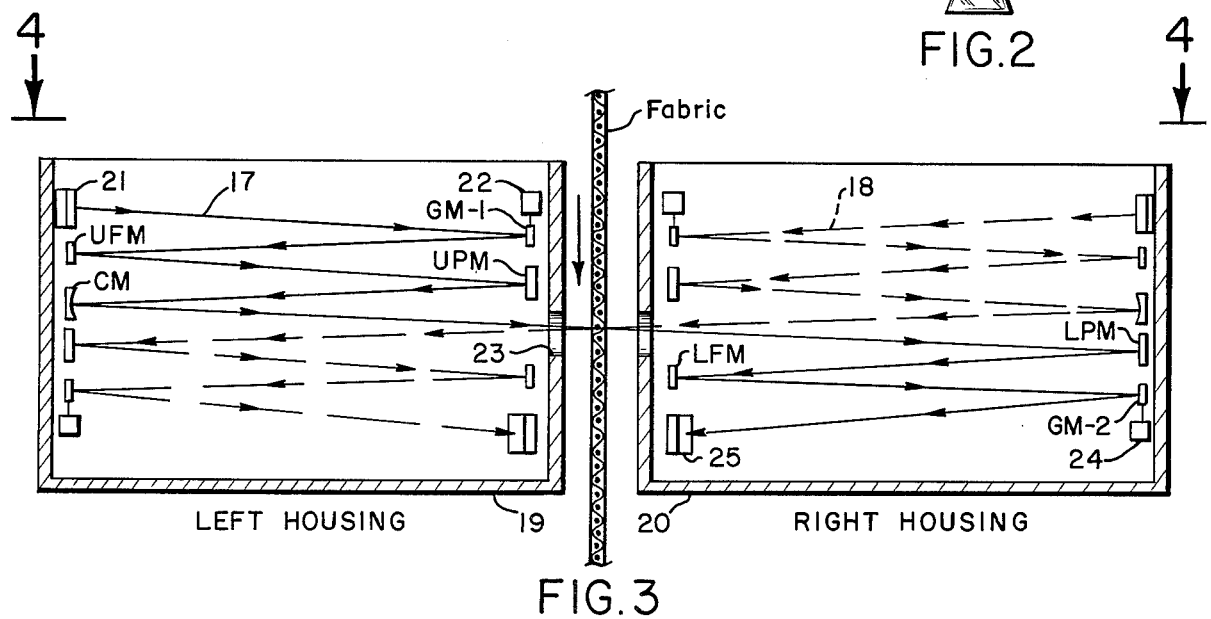
FIG. 3 is a cross section partly in diagrammatic form taken in the direction of the arrows 3—3 of FIG. 1.

All of the foregoing will be better understood by now referring to the cross section of FIG. 3 of the left and right housings, 19 and 20. In FIG. 3, the coherent light beam 17 is shown in solid lines while the path of the switched coherent light beam 18 is indicated by dashed lines.

Referring again to the left housing, the 45° mirror 21 is shown directing the incoming coherent light beam 17 to the left scanning mirror GM-1. The beam reflected from this mirror then passes to the upper fold mirror UFM which in turn directs the beam successively to the plurality of upper plane mirrors UPM. It will be understood that the scanning of the beam takes place in a plane perpendicular to the plane of the drawing of FIG. 3.

From the upper plane mirrors UPM, the beam then is successively passed to the concave mirrors CM and from these mirrors successively directed through the outlet slot 23 across the width of the fabric.

Referring to the lower portion of the right housing, the successive beams are received by the lower plane mirrors LPM from whence they reflect to the lower fold mirror LFM to be received in the de-scanning mirror GM-2. Since the de-scanning mirror GM-2 is synchronized with the scanning of the scanning mirror GM-1, the beam reflected from the de-scanning mirror will only exhibit a very slight movement during each successive reflection. The 45° mirror has a sufficiently large surface to accommodate this movement and direct the beam through L2 to the detector 26 as described in FIG. 1.

Considering now the path of the switched coherent beam 18, this beam will follow the counterparts to the various optical elements described for the left housing as indicated by the dashed beam lines to pass back through the fabric and slot 23 in the left housing wherein the same is de-scanned by components identical to that described for the right housing.

Figure 4:
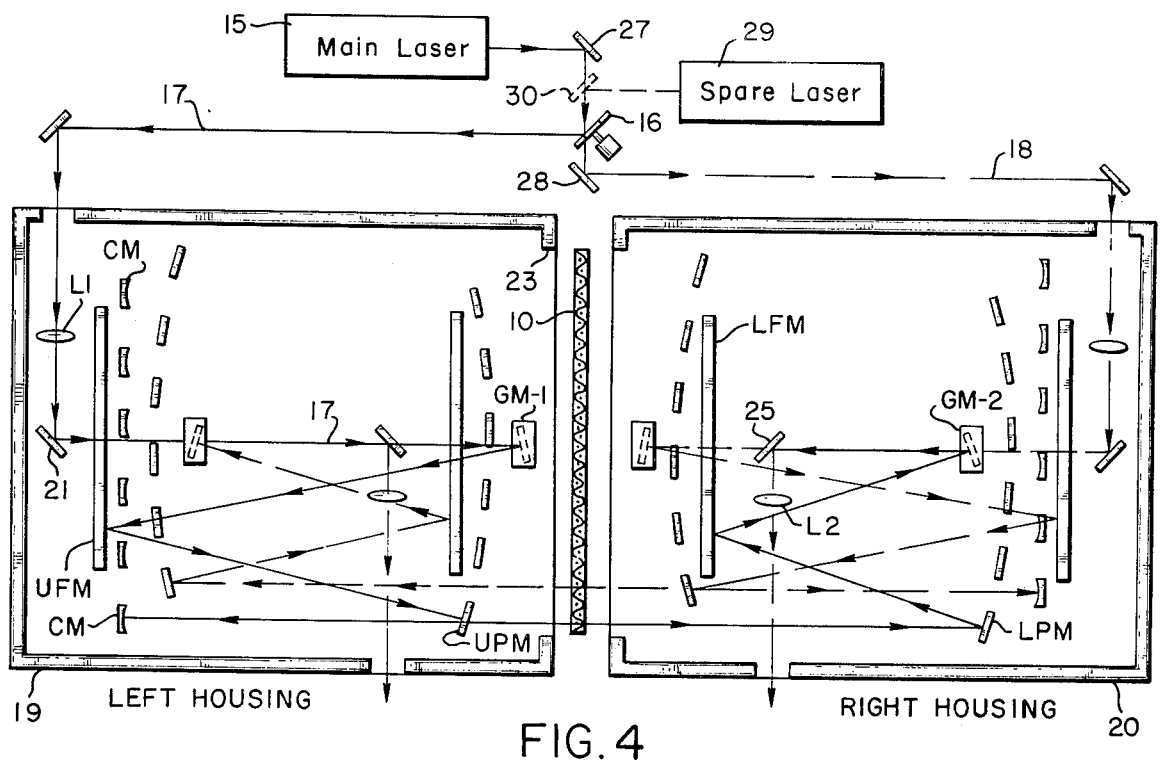
FIG. 4 is a top plan view looking in the direction of the arrows 4—4 of FIG. 3 but illustrating various components exploded forwardly for purposes of clarity.

Reference to the plan view of the left and right housings as schematically depicted in FIG. 4 will further clarify the foregoing described scanning operations. In FIG. 4, the coherent beam entering the left housing is again indicated by a solid line whereas the coherent switched beam 18 entering the right housing is shown as a dashed line. Further, the left scanning mirror GM-1 is shown in an extreme scan position at which the coherent beam is passed through the fabric 10 at the right edge or lower edge as viewed in FIG. 4.

Starting at the upper central portion of FIG. 4, the main laser is shown at 15 together with a first 45° mirror 27 for directing the beam through the beam switch means 16. When one of the four mirrors of the beam switch 16 as described in FIG. 2 intercepts the beam from the mirror 27, it is directed as a coherent beam along the solid line 17 as shown. When the beam from the 45° mirror 27 passes between the mirrors of the beam switch 16, it is in turn reflected by a second 45° mirror 28 to pass to the right as indicated by the dashed coherent beam line 18.

In both FIGS. 1 and 4 there is illustrated a spare laser 29 positioned close to the beam switch 16. This spare laser is so oriented that by positioning an auxiliary 45° mirror 30 shown in phantom lines, its beam will be directed through the beam switch means 16 in the event the main laser 15 should fail.

Still referring to the plan view of FIG. 4, the various mirror arrangements described in FIG. 1 as stated are shown exploded outwardly from the inside opposite end walls of the housing for purposes of clarity. Thus, it will be noted that the coherent beam 17 after passing through the relay lens L1 and being reflected from the 45° mirror 21 passes to the scanning mirror GM-1. At the particular moment of time under consideration, the scanning mirror is at an extreme scan position wherein the beam will be reflected to the upper fold mirror UFM and thence to the upper plane mirror UPM constituting the first mirror in this horizontal row of upper plane mirrors. It will be noted that the horizontal row of upper plane mirrors are oriented when viewed in plan such that when the beam is successively reflected from these mirrors through a scanning operation, it will successively be directed in parallel directions or channels towards the corresponding concave mirror CM in alignment therewith.

From the extreme positioned concave mirror CM at the lower left of the drawing of FIG. 4 in the left housing, the beam passes to the right beneath the upper plane mirror and through the slot 23 and fabric to be received on the correspondingly aligned lower plane mirror LPM in the de-scanning optical portions in the lower portion of the right housing 20. Continuing to trace the solid line path of the beam, it will thence be directed to the lower fold mirror LFM and thence to the de-scanning mirror GM-2. The reflected beam from the de-scanning mirror is then directed by the 45° mirror 25 through the transform lens L2 out of the right housing to the detector 26 as described in FIG. 1.

It will be noted in FIG. 4 that the row of lower plane mirrors LPM are oriented so that the successive parallel directions of the beam will be successively properly reflected towards the lower fold mirror to the de-scanning mirror GM-2. Further the rows of upper and lower plane mirrors follow arcs such that the optical path lengths between GM-1 and GM-2 for each successive reflection are equal.

Since GM-2 is synchronized with GM-1, the direction of the beam after successive reflections throughout a single scan from GM-2 will always be directed towards the 45° mirror 25. However, there will be a slight movement across the mirror 25 for each successive reflection, such movement being in the same direction and resulting from the continuous motion of GM-2 during each successive reflection. The lens L-2 reimages the diffraction pattern occuring in the vicinity of GM-2 on to the detector so that the effect of this slight motion is eliminated at the detector.

The path for the switched coherent beam 18 entering the right housing in FIG. 4 is the same as that described for the beam 17 in the left housing except that the mirrors corresponding to the upper plane mirrors UPM and concave mirrors CM are offset horizontally or upwardly slightly as viewed in FIG. 4 such that the dashed beam passes back through the fabric 10 when the scanning is in its extreme position adjacent to the solid beam path. Similarly, the mirrors in the lower portion of the left housing for de-scanning the dashed beam corresponding to the lower plane mirrors LPM are horizontally offset to be in alignment to receive the dashed beam 18 passing back through the fabric 10.

It should be understood that the solid and dotted line showings for the beams in FIG. 4 are merely paths when the scanning from one side is in an extreme position and the scanning from the other side is an extreme position. Actually, the coherent light beam is passed to the right housing by the beam switch means 16 during half of each complete oscillation of the left scanning mirror GM-1 and de-scanning mirror GM-2. Similarly, the coherent beam is passed to the left housing by the beam switch means only during half of each complete oscillation of the right scanning mirror and associated de-scanning mirror so that the beam scans alternately from the housings in only one direction from one edge of the fabric to the other. The scan from one housing is thus blanked by the beam switch means during the time of scan from the other housing, the scanning mirror in the one housing returning to an initial position while scanning takes place from the other housing.

In the embodiment disclosed, the scanning takes place from the left edge of the fabric to the right edge of the fabric as viewed in FIG. 1, the successive areas along the width of the fabric from the left scanning taking place and then a subsequent scanning from the opposite side taking place to provide successive areas in between the first mentioned areas so that a complete 100% coverage of the fabric is assured.

Figure 5:
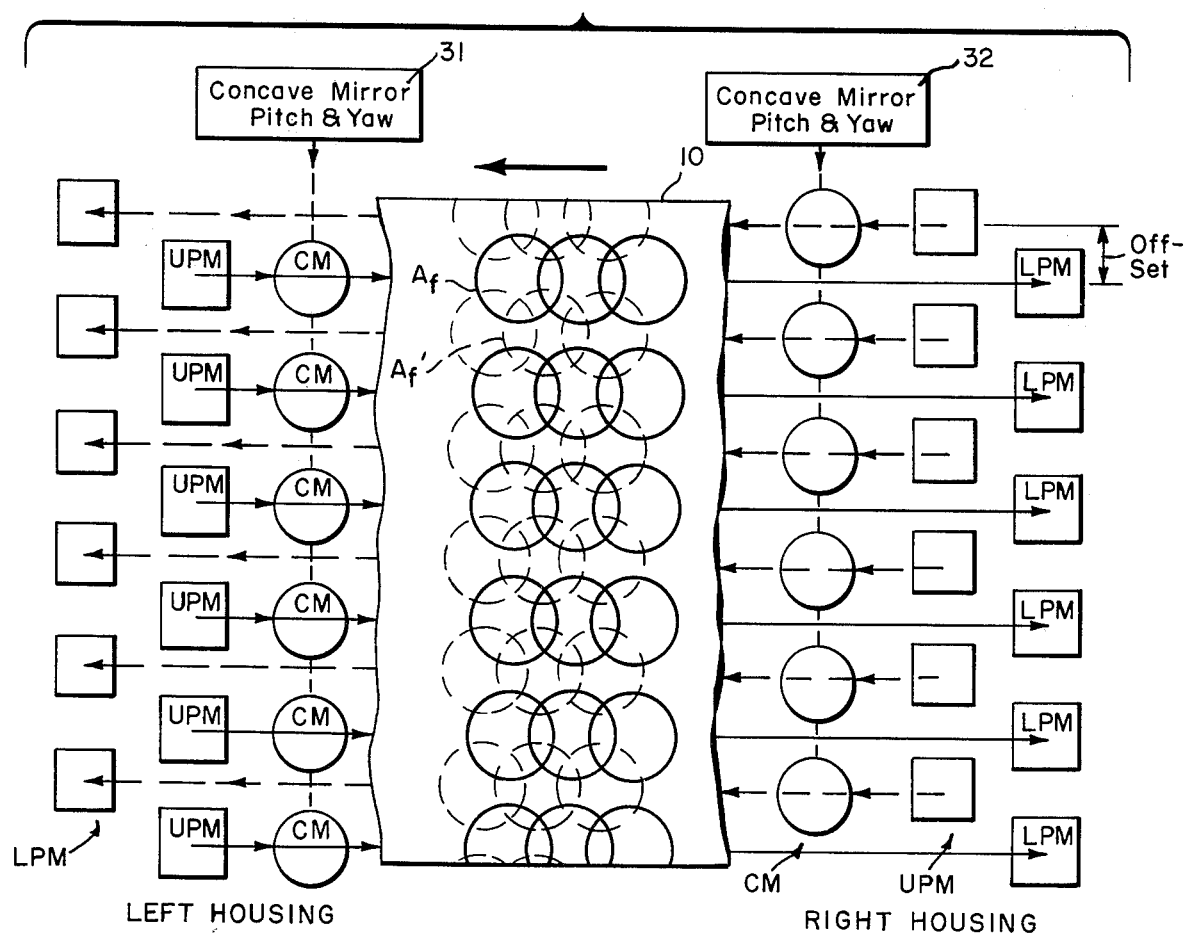
FIG. 5 is a schematic diagram useful in illustrating the alignment of various optical components utilized in the system of FIG. 1; and, FIG. 6 is an overall block diagram illustrating optical paths and electrical connections of the basic components making up the scanning system.

FIG. 5 is a diagramatic illustration of the upper plane mirrors UPM, the concave mirrors CM, and the lower plane mirrors LPM for the left and right housings illustrating the proper alignment for scanning of the fabric 10. Also shown in FIG. 5 in fragmentary view is a portion of the fabric 10 illustrating successive areas through which the coherent beam passes. In this showing, the solid line circles designated Af illustrate the successive areas of positions of the coherent light beam from the left housing while the dashed circles Af' designate the areas through which the coherent light beam passes from the right housing. The spacing between the successive areas is such that they overlap to assure the referred to 100% coverage of the fabric 10 as it moves between the housings.

Still referring to FIG. 5, it will be noted that the left upper plane mirrors and left concave mirrors designated UPM and CM respectively for the left housing are in exact alignment with each other and with the solid circles enclosing the area Af of the fabric 10, the corresponding lower plane mirrors LPM in the lower part of the right housing being similarly aligned. The analogous upper plane mirrors and concave mirrors in the right housing which rows are indicated simply by the arrows UPM and CM in FIG. 5, are exactly aligned with each other and the dashed circles enclosing the areas Af' and also aligned with the corresponding lower plane mirrors in the lower portion of the left housing, the row of these mirrors being designated by the arrow LPM. The offset in a horizontal direction wherein the horizontal plane is considered to be the plane of FIG. 5 is indicated at the upper right of this drawing.

In order to avoid missing any area of the fabric as it vertically moves between the housings as described in FIG. 1, it is important to synchronize the rate of scanning with the fabric transport means 13 described in FIG. 1. The fabric transport is designed to continuously move the fabric vertically downwardly. Means are provided for synchronizing the rate of scanning with this fabric movement such that after each horizontal scan, a next horizontal scan will start immediately vertically above the first scan. This situation is again depicted by various circles Af and Af' in FIG. 5 it being understood that these circles represent successively radiated areas in a horizontal direction which when drawn as illustrated in FIG. 5 will appear to slant slightly as a result of the motion of the fabric in a vertical direction.

In FIG. 5 there is schematically shown above the concave mirrors CM for the left and right housings blocks 31 and 32 which represent a plurality of individual motor means connected respectively to the plurality of individual left concave mirrors and right concave mirrors to enable each of the concave mirrors to be individually initially oriented in pitch and yaw. With this arrangement, periodic alignment of the mirrors can be remotely carried out by energizing these motors with appropriate signals if necessary.

Figure 6:
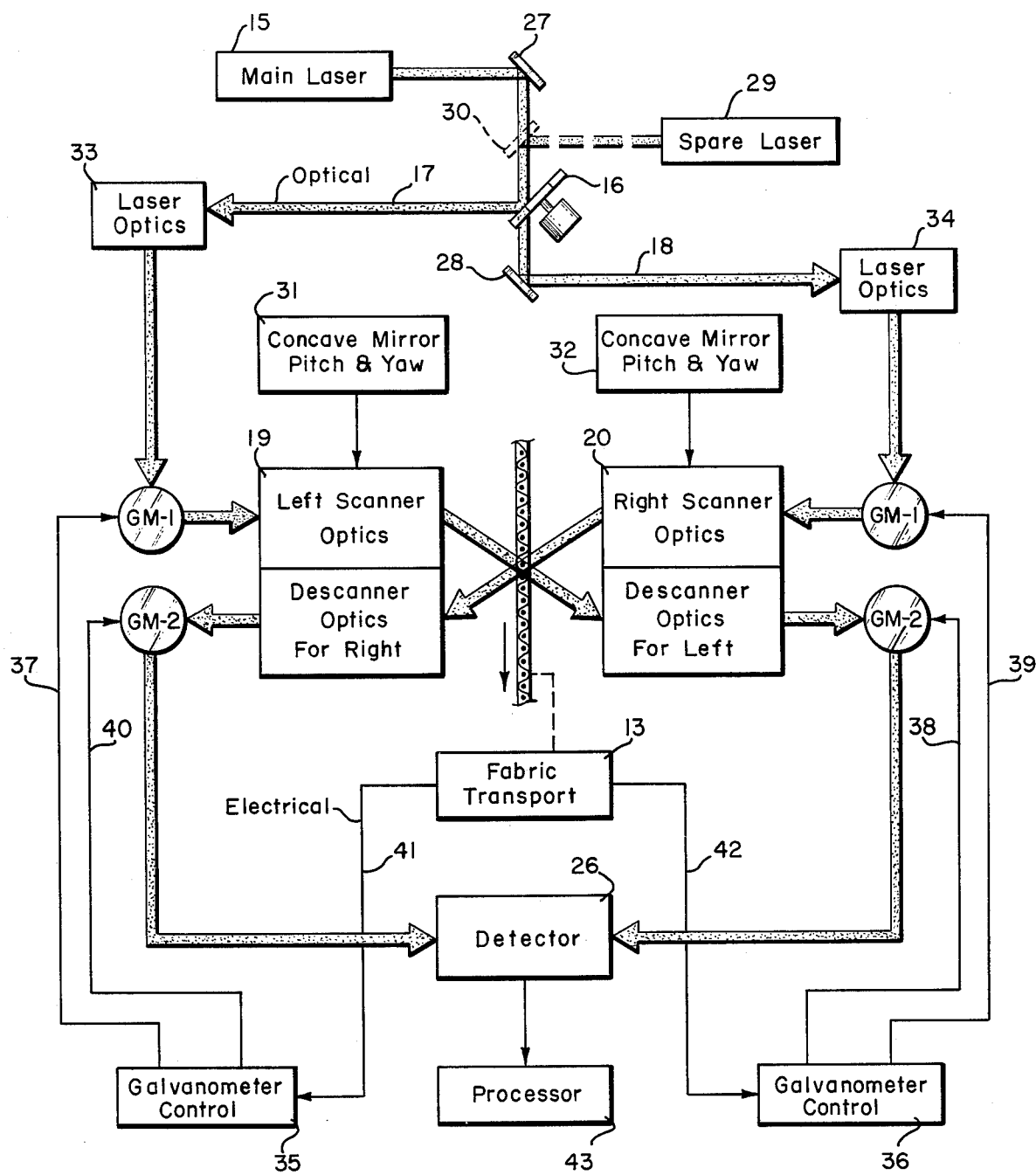

Referring now to the overall block diagram of FIG. 6, the operation of the scanning system of this invention as described can be comprehensibly summarized. In FIG. 6, the optical paths of the coherent light beam are indicated by the double lines and electrical connections between various components indicated by single solid lines.

Thus, in the central portion of FIG. 6 is illustrated the fabric 10 with the left and right housings 19 and 20 shown on either side and separated into upper and lower blocks. The upper block of the left housing 19 incorporates the left scanner optics while the lower block of the right housing 20 incorporates the de-scanner optics therefor. Similarly, the upper block for the right housing incorporates the right scanner optics and the lower block of the left housing incorporates the cooperating de-scanner optics. The direction of movement of the fabric 10 by the fabric transport 13 is downwardly as indicated by the arrow in FIG. 6.

Shown in the upper portion of FIG. 6 is the main laser 15 together with the appropriate 45° mirrors and beam switch means 16 for providing the coherent beam 17 through appropriate laser optics 33 to the left scanning mirror GM-1. The light beam then passes through the left scanner optics through the fabric 10, to the de-scanner optics in the right housing wherein de-scanning is accomplished by the de-scanning mirror GM-2, the beam being passed to the detector 26.

Similarly, the coherent switched beam 18 from the beam switch means 16 is directed through laser optics 34 to the right scanning mirror GM-1, right scanner optics, through the fabric 10 to the de-scanner optics and de-scanning mirror GM-2 from whence the beam is directed to the detector 26.

The scanning and de-scanning mirrors for each of the scanning systems may constitute galvanometers which are appropriately synchronized as by galvanometer controls depicted by the blocks 35 and 36 connecting to the galvanometers through the lines 37 and 38 to synchronize GM-1 in the upper portion of the left housing with GM-2 in the lower portion of the right housing and through lines 39 and 40 to synchronize the right scanning mirror GM-1 in the right housing with the de-scanning mirror GM-2 in the left housing. The respective cooperating scanning and de-scanning galvanometers are locked in frequency and phase to assure that proper de-scanning can take place.

Also shown in FIG. 6 is synchronization of the fabric transport 13 with these galvanometer controls 35 and 36 through connecting lines 41 and 42.

The received coherent light beams in the detector 26 are combined and through appropriate detector optics processed in a suitable processor block 43 to provide appropriate data enabling grading of the quality of the fabric.

As previously mentioned herein, should the main laser 15 fail for any reason, the spare laser 29 may be immediately energized and an appropriate 45° mirror indicated by the phantom line 30 in FIG. 6 positioned to direct the light from the spare laser to the beam switch means 16.

It should be understood in all of the foregoing description that the upper and lower folding mirrors UFM and LFM are provided merely to fold the light path and enable the overall dimensions of the left housing and right housing to be decreased for a given total light path length within each housing. The presence of these folding mirrors is not essential to the operation of the scanning system but certainly desirable in the preferred embodiment in realizing a practical and feasible structure.

It should also be understood that the expressions "vertical," and "horizontal" as used herein are not to be deemed as fixing the orientation of the scanning system but are merely used as convenient orientation terms. Clearly the scanning system could be oriented with the fabric running in a horizontal plane and the beam traversing substantially vertically through the fabric.

In addition, while the preferred embodiment has described various optical components as constituting mirrors, optical elements performing equivalent functions such as lenses or prisms could be used.

In the particular embodiment illustrated in the drawings, there is illustrated six upper plane mirrors in a row for each scanning arrangement and six concave mirrors in a row for each scanning arrangement. If the fabric has a substantial width it will be understood that many more mirrors could be added and the scan angle varied to accommodate the additional mirrors or the scanning mirror displaced further away from the row of mirrors to accommodate any such additional mirrors thereby increasing the width of the overall scan.

The coherent scanning system for fabric inspection is accordingly not to be thought of as limited to the specific embodiment set forth for illustrative purposes.

What is claimed is:

1. A coherent scanning system for inspecting a given area of fabric by analysis of the diffraction pattern developed by a single coherent light beam passed through said fabric wherein the cross-sectional area of the light beam is substantially less than said given area including:
   a. a scanning mirror receiving said coherent light beam and mounted for repeated swinging movement through a given scan angle;
   b. a plurality of first optical means in side-by-side relationship successively receiving said light beam from said scanning mirror and directing it in successive side-by-side parallel directions towards said fabric to irradiate successive areas of said fabric covering said given area;
   c. a de-scanning mirror adapted to swing through said given scan angle; and
   d. a plurality of second optical means in side-by-side relationship in alignment with said first optical means respectively for successively receiving said beam after passing through said successive areas of fabric and successively directing the beam to said de-scanning mirror as it swings through said scan angle so that the beam reflected from said de-scanning mirror can be analyzed.

2. A system according to claim 1, including means for frequency and phase locking the swinging movement of the scanning and de-scanning mirrors.

3. A system according to claim 1, in which said plurality of first optical means includes a row of plane mirrors in side-by-side relationship positioned to successively receive light from said scanning mirror and a row of concave mirrors positioned to respectively receive light succesively reflected from said plane mirrors and successively direct said light in said side-by-side parallel directions towards said fabric, said plurality of second optical means including a row of plane mirrors in side-by-side relationship respectively in alignment with said concave mirrors and oriented to successively reflect said light beam received from said concave mirrors to said de-scanning mirror.

4. A coherent scanning system for inspecting fabric of a given horizontal width while supported in a vertical plane including, in combination:
   a. a coherent light beam source;
   b. a left housing positioned on the left side of said vertical plane including a left scanning mirror receiving said light beam, means for oscillating said mirror about a vertical axis through a given scan angle, a plurality of individual left upper plane mirrors positioned on a horizontal row and oriented to successively receive said light beam reflected from said scanning mirror as it swings through said given scan angle and direct said beam in successive parallel directions generally normal to said vertical plane, and a plurality of individual left concave mirrors positioned on a horizontal row in alignment with said parallel directions to successively receive said light beams reflected from said plurality of upper plane mirrors respectively and direct said beam towards said vertical plane such that successive areas in a horizontal row across the width of the fabric in said plane are exposed to said light beam;
   c. a right housing positioned on the right side of said vertical plane including a de-scanning mirror, means for oscillating said de-scanning mirror about a vertical axis through said given scan angle in synchronism with said left scanning mirror, and a plurality of lower plane mirrors positioned in a horizontal row and oriented to successively receive said light beam from said left concave mirrors after passing through said vertical plane and reflecting said light beam to said de-scanning mirror as it swings through said given scan angle; and
   d. detector means receiving said light beam from said de-scanning mirror for analyzing time sequential diffraction patterns developed by said beam in passing through fabric in said vertical plane for discerning defects in the fabric material.

5. A system according to claim 4, in which said left housing and right housing further include beam folding mirrors between said left scanning mirror and left upper plane mirrors and between said lower plane mirrors and de-scanning mirror to decrease the overall dimensions of the left housing and right housing necessary to accommodate the total length of the light paths therein.

6. A system according to claim 4, in which said scan angle is sufficient to assure that the complete horizontal width of fabric positioned in said vertical plane is scanned and wherein there is provided, in combination, fabric transport means for continuously moving said fabric vertically downwardly; and means for synchronizing the rate of scanning with said fabric transport means such that after each horizontal scan, a next horizontal scan will start above the first scan whereby all of the area of a continuously moving fabric will be inspected.

7. A system according to claim 4, in which said left housing includes a plurality of individual motor means connected respectively to said plurality of individual left concave mirrors to enable each of said concave mirrors to be individually oriented in pitch and yaw whereby automatic alignment of the mirrors can be remotely carried out by energizing said motors with appropriate signals.

8. A system according to claim 4, in which said coherent light source includes a beam switch means to switch the coherent light beam back and forth at a given frequency between said left housing and right housing, said right housing including a right scanning mirror receiving said coherent light beam when passed thereto by said beam switch means, a plurality of individual right upper plane mirrors, and a plurality of individual right concave mirrors all functioning in the same manner as said left scanning mirror, left upper plane mirrors, and left concave mirrors but facing in opposite directions and offset horizontally to successively pass said coherent beam through said vertical plane in an opposite direction such that successive areas in a horizontal row across the width of the fabric in said vertical plane falling between the first mentioned successive areas respectively are exposed to said coherent light beam, said left housing including a de-scanning mirror, and a plurality of individual lower plane mirrors all functioning in the same manner as said first mentioned de-scanning mirror and first mentioned lower plane mirrors but facing in opposite directions and offset horizontally to successively receive said coherent light beam after passing through said vertical plane in said opposite direction and reflect said light beam to said second mentioned de-scanning mirror, said detector means receiving said coherent light beam for analysis thereof.

9. A system according to claim 8, in which the coherent light beam is passed to the right housing by said beam switch means during half of each complete oscillation of said left scanning mirror and first mentioned de-scanning mirror, and passed to said left housing by said beam switch means during half of each complete oscillaton of said right scanning mirror and second mentioned de-scanning mirror so that said beam scans alternately from the housings in only one direction from one edge of the fabric to the other, the scan from one housing being blanked by the beam switch means during the time of scan from the other housing.

10. A system according to claim 8, in which said coherent light source comprises a main laser providing the coherent beam; a 45° plane mirror receiving the coherent beam from said main laser and directing it towards said beam switch means; and wherein there is provided a spare laser in a fixed position such that in the event of failure of said main laser an additional 45° mirror may be positioned in front of said spare laser to direct its coherent beam towards said beam switch means.

* * * * *